United States Patent [19]
Hodge

[11] Patent Number: 5,486,178
[45] Date of Patent: Jan. 23, 1996

[54] FEMORAL PREPARATION INSTRUMENTATION SYSTEM AND METHOD

[76] Inventor: W. Andrew Hodge, 120 Clarke Ave., Palm Beach, Fla. 33480

[21] Appl. No.: 197,387

[22] Filed: Feb. 16, 1994

[51] Int. Cl.⁶ .................................................. A61B 17/56
[52] U.S. Cl. ...................... 606/82; 606/88; 606/102
[58] Field of Search .................... 606/88, 87, 89, 606/96, 102, 86, 79, 80, 82; 523/20, 18; 33/511, 512

[56] References Cited

U.S. PATENT DOCUMENTS

| | | | |
|---|---|---|---|
| 4,474,177 | 10/1984 | Whiteside | 606/88 X |
| 4,567,886 | 2/1986 | Peterson | 606/88 |
| 4,703,751 | 11/1987 | Pohl | 606/62 |
| 4,722,330 | 2/1988 | Russell et al. | 606/88 |
| 4,759,350 | 7/1988 | Dunn et al. . | |
| 5,035,700 | 7/1991 | Kenna | 606/88 |
| 5,037,423 | 8/1991 | Kenna | 606/88 |
| 5,122,144 | 6/1992 | Bert et al. | 606/88 |

FOREIGN PATENT DOCUMENTS

| | | | |
|---|---|---|---|
| 380451 | 8/1990 | European Pat. Off. . | |
| 538153 | 4/1993 | European Pat. Off. | 606/88 |
| 2679766 | 2/1993 | France . | |

OTHER PUBLICATIONS

Scott et al. "P.F.C. Modular Knee System . . . Instruments" Johnson & Johnson Orthopaedics brochure, (date unknown).
MGII Total Knee System Surgical Technique, Zimmer (undated) author unknown, pp. 1–40.

Primary Examiner—Stephen C. Pellegrino
Assistant Examiner—Guy V. Tucker
Attorney, Agent, or Firm—Samuelson & Jacob

[57] ABSTRACT

A femoral preparation instrumentation system and method employs a multi-purpose sizing guide for placement at the distal femur, secured to an intramedullary alignment rod seated within the femur, enabling the determination of the appropriate size for the femoral knee prosthesis to be implanted and the setting of the axial rotational position of the femoral knee prosthesis, and providing for the accomplishment of preliminary posterior condylar cuts and the location of a distal femoral resection guide at the distal femur, while the sizing guide remains in place at the distal femur.

17 Claims, 4 Drawing Sheets

FEMORAL PREPARATION INSTRUMENTATION SYSTEM AND METHOD

BACKGROUND OF THE INVENTION

1. Field of the Invention

The present invention relates generally to the implant of prosthetic joints and pertains, more specifically, to the preparation of the distal femur for the implant of a femoral knee prosthesis, utilizing a minimal number of individual instruments to assist in establishing the surfaces necessary for locating and securing the prosthesis in place on the femur.

2. Description of the Related Art

The implant of a prosthetic knee joint requires that the distal femur be prepared to receive the femoral component of the knee prosthesis by cutting the bone of the femur to establish accurately located surfaces against which the femoral knee prosthesis will rest upon implant of the prosthesis. Various guide components are available to the surgeon for assisting in determining the appropriate size of the femoral knee prosthesis to be implanted and for guiding a saw blade during use of the saw blade to make the cuts which establish the desired surfaces for effecting the implant. These guide components usually are located and secured upon the distal femur to provide sizing information and to place guide surfaces at appropriate locations and orientation for guiding the saw blade during the execution of a transversely directed distal femoral cut, an axially directed anterior femoral cut, an axially directed posterior femoral cut, an anterior chamfer and a posterior chamfer. Currently available guide components usually require a series of separate guide components secured sequentially to the distal femur to determine sizing and to accomplish the various cuts. Since it is desirable that all of the necessary sizing and cuts be established as quickly as possible, concomitant with safety and accuracy, it would be advantageous to have available a femoral preparation instrumentation system and method which enables all of the required sizing steps and cuts to be executed fully and completely with a minimal number of guide components.

SUMMARY OF THE INVENTION

The present invention provides a femoral instrumentation system and method which enables the execution of all of the necessary sizing steps and cuts, as outlined above, fully and completely, utilizing a minimal number of guide components to maximum advantage, and has several objects and advantages, some of which are summarized as follows: Provides a minimum number of guide components for conducting sizing and for guiding a saw blade during the execution of the cuts necessary to complete the implant of the femoral component of a prosthetic knee joint; Enables added access to the posterior condyles of the distal femur during the implant procedure for ease of accomplishing the necessary implant steps; Provides a multi-purpose femoral sizing and cutting guide component which enables a choice in axial rotational orientation of the femoral knee prosthesis, as well as accurate distal location of the femoral knee prosthesis, utilizing both anterior and posterior referencing, in a single guide component; Enhances the speed and accuracy with which all of the aforesaid sizing and cuts can be accomplished; Enables all of the aforesaid sizing and cuts to be established with an accurately fixed relationship relative to one another; Maintains a predetermined flexion gap by accurately preserving the location of the posterior cuts associated with the predetermined flexion gap; Minimizes the time required for the completion of all of the aforesaid sizing steps and cuts, while maintaining safety, thereby reducing the overall operating time, to the benefit of the patient and the surgeon; Reduces the possibility of error in the choice of size for the femoral component and for the location of the cuts necessary to accommodate the chosen size with accuracy; Is simple and effective in use; Aids in the preservation of the tissue remaining upon completion of the required cuts by minimizing any trauma related to the installation and removal of multiple sizing and cutting guides; Provides a practical and economical construction which is rugged enough to withstand the rigors of use over a long service life, with the preservation of accuracy and ease of use.

The above objects and advantages, as well as further objects and advantages, are attained by the present invention which may be described briefly as a femoral preparation instrumentation system for preparing a femur, at the distal femur thereof, for the implant of a femoral knee prosthesis, the femoral preparation instrumentation system including a femoral sizing guide for placement on an intramedullary alignment rod which is to be seated within the femur and which includes a rod portion for projecting generally axially from the distal femur when the intramedullary alignment rod is seated within the femur, the femoral sizing guide comprising: a sizing guide block; axially projecting foot means on the sizing guide block for engaging the posterior distal femur; block mounting means for mounting the sizing guide block upon the rod portion of the intramedullary alignment rod for selective movement in anterior/posterior directions relative to the rod portion; selective locking means for selectively locking the sizing guide block against movement relative to the rod portion when the sizing block is in a sizing position wherein the foot means of the sizing guide block is located against the posterior distal femur, such that the sizing guide block is selectively locked in place upon the seated intramedullary alignment rod in the sizing position; a stylus for engaging the anterior cortex; stylus mounting means for mounting the stylus upon the sizing guide block for unrestricted movement in anterior/posterior directions relative to the sizing guide block to enable location of the stylus against the anterior cortex with the stylus mounted upon the sizing guide block; size indicator means for providing an indication, when the sizing guide block is in the sizing position and the stylus is located against the anterior cortex, of the size of the femoral knee prosthesis to be implanted; and a posterior femoral cutting guide on the sizing guide block for guiding a cutting instrument to establish a preliminary posterior femoral cut when the sizing guide block is in the sizing position.

Another embodiment of the present invention includes a femoral preparation method for preparing a femur, at the distal femur thereof, for the implant of a femoral knee prosthesis, the femoral preparation method comprising: placing a sizing guide block of a femoral sizing guide on a rod portion of an intramedullary alignment rod, the sizing guide block having thereon axially projecting foot means for engaging the posterior distal femur when the intramedullary alignment rod is seated within the femur with the rod portion projecting generally axially from the distal femur; locating the sizing guide block upon the rod portion in an anterior/posterior direction relative to the rod portion to engage the foot means with the posterior distal femur when the intramedullary alignment rod is seated within the femur, thereby locating the sizing guide block in a sizing position with respect to the distal femur; Locking the sizing guide block against movement relative to the rod portion when the sizing block is in the sizing position wherein the foot means of the sizing guide block is located against the posterior distal femur, such that the sizing guide block is locked in place upon the intramedullary alignment rod in the sizing position; and guiding a cutting instrument with a posterior femoral cutting guide on the sizing guide block to establish a preliminary posterior femoral cut when the sizing guide block is in the sizing position.

BRIEF DESCRIPTION OF THE DRAWING

The invention will be understood more fully, while still further objects and advantages will become apparent, in the following detailed description of preferred embodiments of the invention illustrated in the accompanying drawing, in which.

DESCRIPTION OF THE PREFERRED EMBODIMENTS

Figure 1:
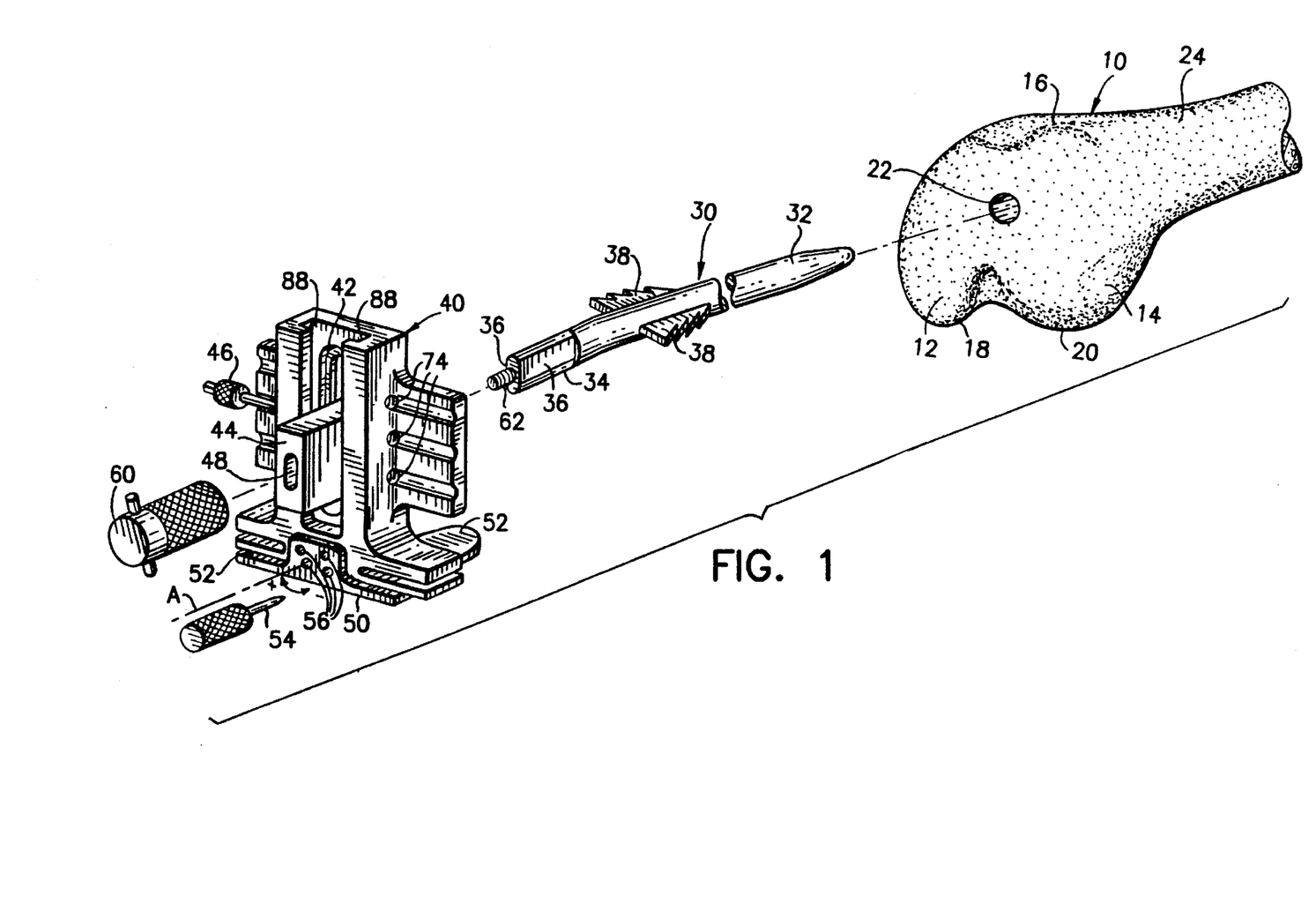
FIG. 1 is an exploded perspective pictorial view showing the placement of a sizing guide constructed in accordance with the present invention at the distal femur, in accordance with the method of the present invention.
Figure 2:
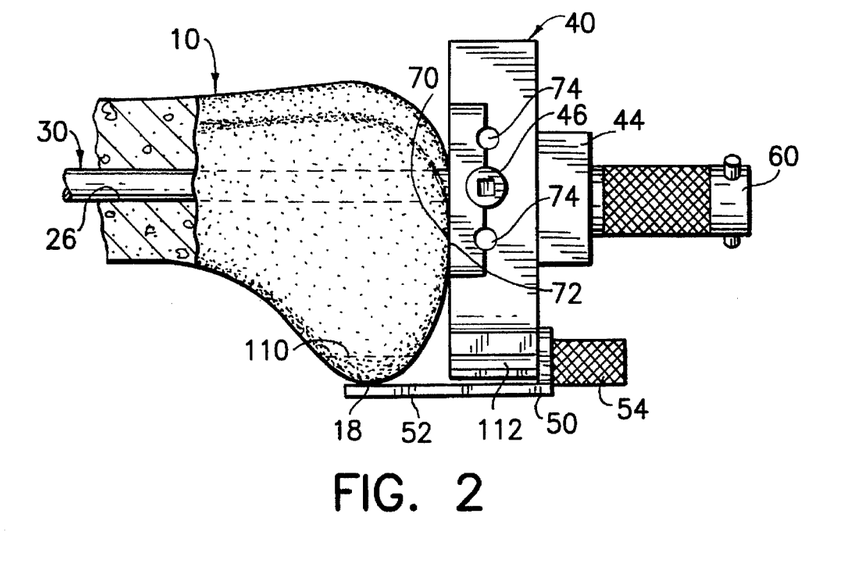
FIG. 2 is a longitudinal elevational view of the distal femur with the sizing guide in place.

Referring now to the drawing, and especially to FIGS. 1 and 2 thereof, the femur of a recipient of a prosthetic knee implant includes a distal femur 10 shown being prepared for the implant of the femoral knee prosthesis (not shown) of the prosthetic knee implant. Distal femur 10 includes condyles 12 and 14, an anterior cortex 16 and posterior surfaces 18 and 20 on the respective condyles 12 and 14. A hole 22 has been drilled in line with the shaft 24 of the femur, in both the sagittal and coronal planes, to enable entry into the distal femoral canal 26 for the reception of an intramedullary alignment rod 30, in a now well-known manner. Intramedullary alignment rod 30 includes an elongate stem 32 for extending generally axially within the femoral canal 26, and a longitudinally extending rod portion in the form of a rod head 34 having essentially flat, opposed flanks 36. Wedge-like barbed wings 38 are integral with the stem 32 of rod 30 beneath the rod head 34, and the head 34 is angled slightly relative to the stem 32 for providing the necessary valgus angle.

A femoral sizing guide includes a sizing guide block 40 having an elongate slot 42, extending transverse to the longitudinal direction of the rod head 34, generally in the altitudinal, or anterior/posterior direction, and a slide 44 is captured in the sizing guide block 40 for sliding movement within the slot 42 to enable relative altitudinal, or anterior/posterior movements between the slide 44 and the sizing guide block 40. Locking means in the form of a set screw 46 selectively locks the sizing guide block 40 and the slide 44 together, against such relative movement. Slide 44 includes a socket 48 which is essentially complementary to the head 34 of rod 30, for purposes which will be described below.

Foot means in the form of a foot member 50 is mounted for pivotal movement relative to the sizing guide block 40 about an axis A, which is essentially normal to the altitudinal, or anterior/posterior direction and to the lateral, or medial/lateral direction, and includes a pair of feet 52 extending in the longitudinal direction, generally parallel to axis A. The pivotal movement of the foot member 50 is between a central, or neutral position wherein the feet 52 extend in a plane generally parallel to the lateral, or medial/lateral direction, and each of two end positions, in which the feet 52 are rotated about axis A relative to the sizing guide block 40 through a small angle in either direction away from the neutral position, as indicated by the + and the − directions in FIG. 1 Typically, the small angle is ±3°, and the foot member 50 is locked at any one of the neutral position, the +3° position, or the −3° position by means of a locking pin 54 placed in selected corresponding aligned locking holes 56 in the foot member 50 and the sizing guide block 40.

The sizing guide block 40 is assembled with the intramedullary alignment rod 30 by inserting the head 34 into the socket 48 and threading a nut 60 onto a thread 62 on the head 34 to capture the sizing guide block 40 on the rod 30, while making certain that the valgus angle of the rod 30 is aligned properly for the left or the right knee. While the foot member 50 is shown in the neutral position, at this juncture the surgeon will choose either the neutral position or one of the rotational positions, illustrated as the +3° or −3° positions, depending upon the condition of the knee and which knee of the recipient is being replaced.

With the set screw 46 loosened to permit relative altitudinal, or anterior/posterior movements between the sizing guide block 40 and the slide 44, the stem 32 of the intramedullary alignment rod 30 is advanced axially slowly into the femoral canal 26 and the sizing guide block 40, which now is assembled with the intramedullary alignment rod 30, is moved axially toward the distal femur 10. Proper depth and rotation of rod 30 about the longitudinal direction is attained when the sizing guide block 40 is fully seated at the distal femur 10, with the feet 52 against the corresponding posterior surfaces 18 and 20 of the condyles 12 and 14 and the rear surface 70 of the sizing guide block 40 against the distal condylar surface 72, as depicted in FIG. 2. As the barbed wings 38 of the rod 30 enter the distal femur 10, proper rotational alignment of the assembled sizing guide block 40 and rod 30 is assured by engagement of the feet 52 with the posterior surfaces 18 and 20, and then is maintained with the assistance of the wings 38 engaged within the distal femur 10. Once the sizing guide block 40 is fully seated upon the distal femur 10, the set screw 46 is tightened to lock the slide 44 and the sizing guide block 40 against relative altitudinal, or anterior/posterior movements. The complementary configurations of the socket 48 in the sizing guide block 40 and the head 34 of rod 30, including the flat flanks 36, preclude relative rotation between the rod 30 and the sizing guide block 40. Locking of the slide 44 and the sizing guide block 40 against altitudinal movement relative to one another is assured by providing several alternate sites 74 for the set screw 46, enabling the set screw 46 to be seated properly against the slide 44 for secure locking in any relative position of the slide 44 and the sizing guide block 40. The sizing guide block 40 thus is secure in a sizing position, for further operations, as follows.

Figure 3:
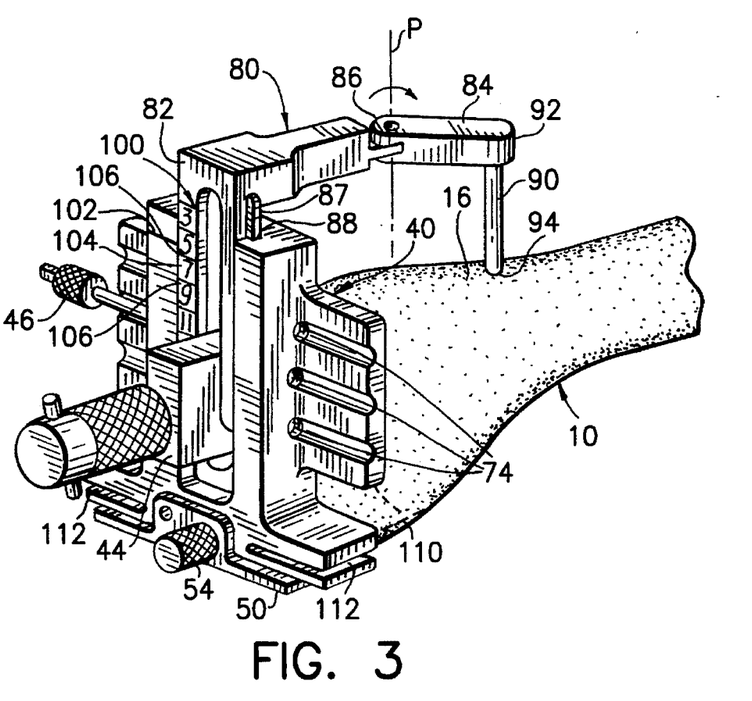
FIG. 3 is a perspective pictorial view showing a sizing stylus and sizing operation in accordance with the invention.

Turning now to FIG. 3, sizing now is accomplished with the aid of a sizing stylus assembly 80 having a bifurcated leg 82 and an arm 84 mounted, at the near end 86 of the arm 84, on the leg 82 for swinging movements about a pivotal axis P. Leg 82 includes rails 87 received within grooves 88 in the sizing guide block 40 such that leg 82 is freely slidable within the grooves 88, in altitudinal, or anterior/posterior directions, the bifurcated construction of the leg 82 enabling the leg 82 to straddle the slide 44 for unrestricted movement within the groove 88. A stylus 90 is carried by the arm 84, at the far end 92 of the arm 84, and is located such that the tip 94 of the stylus 90 will contact the anterior cortex 16 when the leg 82 is engaged within grooves 88, as illustrated. The surgeon then moves the stylus 90 in a lateral, or medial/lateral direction, pivoting the stylus 90 about axis P through a sweeping movement, with the tip 94 of the stylus 90 contacting the anterior cortex 16 to trace the surface contour of the anterior cortex 16. As the tip 94 of the stylus 90 traces the surface contour of the anterior cortex 16, the stylus 90 will be moved in directions normal to the sweeping movement, that is, in altitudinal, or anterior/posterior directions. The altitudinal, or anterior/posterior movements are transmitted to the leg which slides freely in the grooves 88. The movement is observed by the surgeon and is quantified by means of an indicator in the form of a scale 100 on the leg 82 and an index mark 102 on the sizing guide block 40, adjacent the scale 100. The scale 100 is calibrated in the available sizes of femoral knee prostheses, one of which is to be chosen for implant at the distal femur 10. Each size designation 104 is placed between two limit marks 106, along the scale 100. As the stylus 90 is swept across the anterior cortex 16, the index mark 102 should remain within one size designation 104, between the two limit marks 106 designating that one size. In this manner, the appropriate size is determined for the femoral knee prosthesis. Subsequently, preliminary posterior femoral cuts 110 are made by guiding a cutting instrument, such as a saw blade, with posterior femoral guide slots 112 in the sizing guide block 40.

It has been observed that in some instances the index mark 102 does not remain within one size designation 104, between the two limit marks 106 designating that one size, as the stylus 90 is swept laterally across the anterior cortex 16, as described above. Rather, the index mark 102 straddles a limit mark 106 between two adjacent size designations 104 during sweeping movements of the stylus 90. In such an occurrence, the set screw 46 is loosened, subsequent to the completion of the preliminary posterior femoral cuts 110, and the sizing guide block 40 is moved relative to the slide 44, and the rod 30, in the anterior direction until it is observed that the index mark 102 remains within one size designation 104 as the stylus 90 is swept along the anterior cortex 16, thus placing the sizing guide block 40 in an adjusted sizing position. Then, the set screw 46 is tightened to secure the sizing guide block 40 in the adjusted sizing position, and further posterior femoral cuts are made, using the posterior femoral guide slots 112. The further posterior femoral cuts remove only a very minimal amount of additional bone and assure proper sizing for the femoral knee prosthesis of a size selected from the available sizes of femoral knee prostheses.

Figure 4:
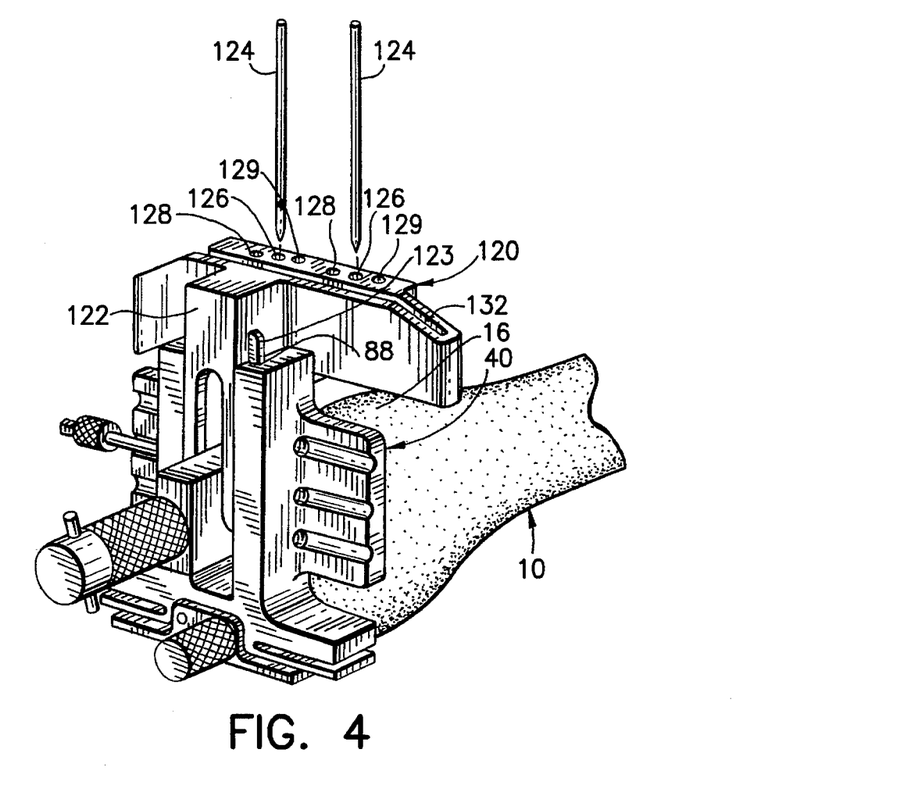
FIG. 4 is a perspective pictorial view showing location of a distal femoral cutting guide.
Figure 5:
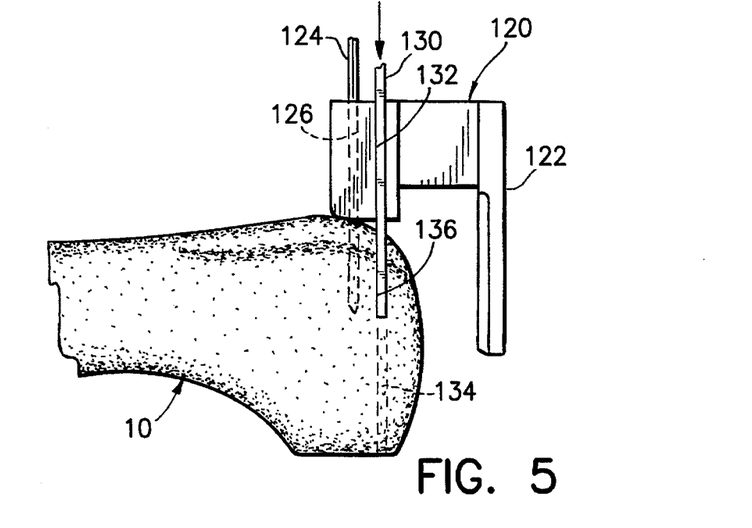
FIG. 5 is a longitudinal elevational view showing the establishment of a distal cut.

Referring now to FIGS. 4 and 5, with the anterior/posterior sizing stylus assembly 80 now removed from the sizing guide block 40, a distal femoral resection guide 120 is assembled with the sizing guide block 40. To this end, distal femoral resection guide 120 includes a bifurcated leg 122, similar in construction to leg 82 of stylus assembly 80, and having rails 123 for reception within the grooves 88 in the sizing guide block 40. Upon insertion of leg 122 into grooves 88, the distal femoral resection guide 120 is seated upon the distal femur 10, as shown in FIG. 4. Locating pins 124 then are inserted through a set of holes 126 in the distal femoral resection guide 120 and are embedded in the bone of the distal femur 10. The set of holes 126 is one of three sets of holes 126, 128 and 129, for purposes which will be set forth below.

Once the locating pins 124 are affixed in the distal femur 10, the distal femoral resection guide 120 is removed from the sizing guide block 40, by slipping the sizing guide block 40 in an anterior direction off the locating pins 124, and then the sizing guide block 40 and the intramedullary alignment rod 30 are removed from the distal femur 10. The distal femoral resection guide 120 is then seated in place upon the distal femur 10 by slipping the resection guide 120 back over the locating pins 124, with the locating pins 124 inserted into any one of the three sets of holes 126, 128 and 129, the appropriate set being selected by the surgeon on the basis of the amount of bone to be removed from the distal end of the femur. Once the resection guide 120 is in place on the distal femur 10, a cutting instrument, shown in the form of saw blade 130, is guided by a cutting guide slot 132 in the resection guide 120 to effect a distal femoral cut 134, as seen in FIG. 5.

Figure 6:
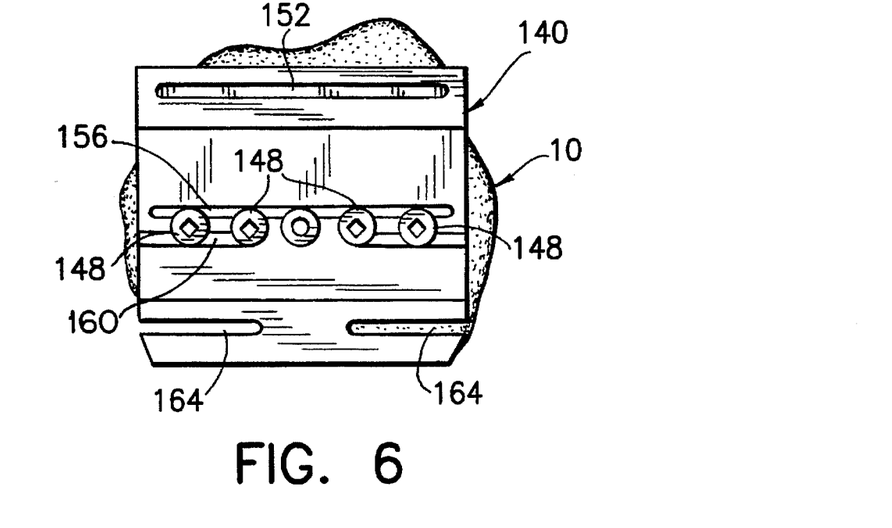
FIG. 6 is an end view showing the placement of a femoral cutting guide at the distal femur.
Figure 7:
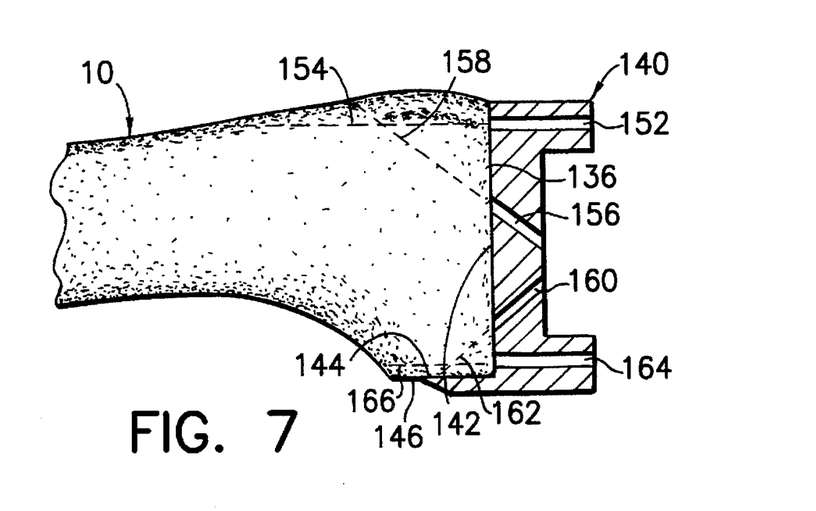
FIG. 7 is a longitudinal elevational view of the distal femur with the femoral cutting guide in place and shown in cross-section.

Upon completion of the distal femoral cut 134, the resection guide 120 is removed to expose the flat distal surface 136. The surgeon then selects a femoral cutting guide 140 corresponding to the selected size of the femoral knee prosthesis to be implanted at the distal femur 10, as determined in the manner described above in connection with the sizing guide block 40, and the femoral cutting guide 140 is affixed to the distal femur 10, against the distal surface 136, as illustrated in FIGS. 6 and 7. The femoral cutting guide 140 is provided with locator means including a first locator surface 142 for engaging the distal surface 136 of the distal femur 10, and a second locator surface 144 essentially normal to the first locator surface 142 and in position to engage the posterior condylar surfaces 146 established by the preliminary posterior cuts 110, or by the further posterior cuts, as described above. Once the first locator surface 142 is seated against the distal surface 136, with the second locator surface 144 engaging the posterior condylar surfaces 146, the surgeon again may assess the anterior/posterior size, as well as the medial/lateral size, of the femoral knee prosthesis to be implanted, based upon the dimensions of the femoral cutting guide 140 and an observation of the relationship between the seated femoral cutting guide 140 and the distal femur 10. The femoral cutting guide 140 then is affixed to the distal femur 10, as by headed pins 148. The affixation of the femoral cutting guide 140 is especially secure by virtue of the intimate contact between the first locator surface 142 and the distal surface 136, and between the second locator surface 144 and the posterior condylar surfaces 146, which intimate contact in two planes provides a high degree of stability and a concomitant high degree of accuracy for the next cuts. The placement of the second locator surface 144 at the posterior condylar surfaces 146 enables increased ease of accurate placement and securement of the femoral cutting guide 140, by virtue of the clear access provided by the preliminary posterior cuts 110.

The femoral cutting guide 140 includes cutting guide slots for completion of the cuts required for the implant of the femoral knee prosthesis. Thus, a cutting instrument, such as a saw blade, is guided by an anterior guide slot 152 for completing an anterior cut 154, then by an anterior chamfer guide slot 156 for completing an anterior chamfer cut 158, then by a posterior chamfer guide slot 160 for completing a posterior chamfer cut 162, and then by posterior guide slots 164 for completing final posterior cuts 166. The femoral cutting guide 140 then is removed from the distal femur 10, which now is prepared for the implant of the femoral knee prosthesis. It is noted that by employing the posterior condylar surfaces 146 as reference surfaces against which the femoral cutting guide 140 is located, a predetermined flexion gap is maintained by virtue of the accurate preservation of the location of the preliminary posterior condylar cuts 110 and the subsequent location of the final posterior cuts 166, which final posterior cuts 166 are associated with the flexion gap.

The sizing guide block 40 may be characterized as a multi-purpose component in that the sizing guide block 40 remains in place upon the distal femur 10 during sizing and during the execution of the preliminary posterior cuts 110, as well as any further posterior cuts which may be necessary for accurate sizing, as described above. The posterior cuts provide a degree of access to the posterior femoral condyles heretofore unavailable in a simplified instrumentation system, enabling the removal of any posterior osteophytes and facilitating the correct fitting of the femoral knee prosthesis to be implanted. The multiple functions enabled by the sizing guide block 40 reduce the total number of components required in the instrumentation system of the present invention, and simplifies the procedure by eliminating the necessity for installing and removing a greater number of instrument components.

It will be seen that the present invention attains the objects and advantages summarized above, namely: Provides a minimum number of guide components for conducting sizing and for guiding a saw blade during the execution of the cuts necessary to complete the implant of the femoral component of a prosthetic knee joint; Enables added access to the posterior condyles of the distal femur during the implant procedure for ease of accomplishing the necessary implant steps; Provides a multi-purpose femoral sizing and cutting guide component which enables a choice in axial rotational orientation of the femoral knee prosthesis, as well as accurate distal location of the femoral knee prosthesis, utilizing both anterior and posterior referencing, in a single guide component; Enhances the speed and accuracy with which all of the aforesaid sizing and cuts can be accomplished; Enables all of the aforesaid sizing and cuts to be established with an accurately fixed relationship relative to one another; Maintains a predetermined flexion gap by accurately preserving the location of the posterior cuts associated with the predetermined flexion gap; Minimizes the time required for the completion of all of the aforesaid sizing steps and cuts, while maintaining safety, thereby reducing the overall operating time, to the benefit of the patient and the surgeon; Reduces the possibility of error in the choice of size for the femoral component and for the location of the cuts necessary to accommodate the chosen size with accuracy; Is simple and effective in use; Aids in the preservation of the tissue remaining upon completion of the required cuts by minimizing any trauma related to the installation and removal of multiple sizing and cutting guides; Provides a practical and economical construction which is rugged enough to withstand the rigors of use over a long service life, with the preservation of accuracy and ease of use.

It is to be understood that the above detailed description of preferred embodiments of the invention is provided by way of example only. Various details of design, construction and procedure may be modified without departing from the true spirit and scope of the invention, as set forth in the appended claims.

The embodiments of the invention in which an exclusive property or privilege is claimed are defined as follows:

1. An improvement in a femoral preparation instrumentation system for preparing a femur, at the distal femur thereof, for the implant of a femoral knee prosthesis, the femoral preparation instrumentation system including an intramedullary alignment rod and a femoral sizing guide for placement on the intramedullary alignment rod which is to be seated generally axially within the femur and which includes a rod portion for projecting from the distal femur in a longitudinal direction when the intramedullary alignment rod is seated within the femur, the improvement comprising:

a sizing guide block;

axially projecting foot means on the sizing guide block for engaging the posterior distal femur;

block mounting means for mounting the sizing guide block upon the rod portion of the intramedullary alignment rod for selective movement in altitudinal directions relative to the longitudinally directed rod portion, the block mounting means including engaging means for precluding rotation of the sizing guide block relative to the rod portion about the longitudinal direction when the sizing guide block is mounted upon the rod portion;

selective locking means for selectively locking the sizing guide block against altitudinal movement relative to the rod portion when the sizing block is in a sizing position wherein the foot means of the sizing guide block is located against the posterior distal femur, such that the sizing guide block is selectively locked in place upon the seated intramedullary alignment rod in the sizing position;

a stylus for engaging the anterior cortex;

stylus mounting means for mounting the stylus upon the sizing guide block for unrestricted movement in altitudinal directions relative to the sizing guide block to enable location of the stylus against the anterior cortex with the stylus mounted upon the sizing guide block;

size indicator means for providing an indication, when the sizing guide block is in the sizing position and the stylus is located against the anterior cortex, of the size of the femoral knee prosthesis to be implanted; and a posterior femoral cutting guide on the sizing guide block for guiding a cutting instrument to establish a preliminary posterior femoral cut when the sizing guide block is in the sizing position.

2. The invention of claim 1 wherein the stylus mounting means includes pivotal means for mounting the stylus for sweeping movement in a lateral direction across the anterior cortex, while the stylus is free to move in the altitudinal directions in response to the sweeping movement.

3. The invention of claim 1 wherein the foot means includes a pair of longitudinally projecting feet providing one foot for engaging each corresponding femoral condyle of the distal femur.

4. The invention of claim 1 including:

rotational means mounting the longitudinally projecting foot means on the sizing guide block for selective rotation about the longitudinal direction relative to the sizing guide block; and foot locking means for locking the foot means in a selected position about the longitudinal direction relative to the sizing guide block to select a particular rotational position for the femoral knee prosthesis to be implanted.

5. The invention of claim 4 wherein the foot means includes a pair of longitudinally projecting feet providing one foot for engaging each corresponding femoral condyle of the distal femur.

6. The invention of claim 1 wherein the femoral instrumentation system includes:

a distal femoral resection guide for guiding a cutting instrument to establish a distal femoral cut; and locator means on the sizing guide block for locating the distal femoral resection guide on the distal femur for accomplishing the distal femoral cut.

7. The invention of claim 6 wherein the femoral instrumentation system includes a femoral cutting guide comprising:

locator means on the femoral cutting guide for fully locating the femoral cutting guide upon the distal femur as prepared with the preliminary posterior cut and the distal femoral cut;

securing means for securing the fully located femoral cutting guide upon the distal femur; and guide means on the femoral cutting guide for guiding a cutting instrument to establish a final posterior cut, an anterior cut, an anterior chamfer cut and a posterior chamfer cut.

8. The invention of claim 7 wherein the locator means includes a first locator surface for engaging the distal femoral cut and a second locator surface for engaging the preliminary posterior femoral cut.

9. An improvement in a femoral preparation method for preparing a femur, at the distal femur thereof, for the implant of a femoral knee prosthesis, the improvement comprising:

placing a sizing guide block of a femoral sizing guide on a longitudinally directed rod portion of an intramedullary alignment rod with the sizing guide block fixed against rotation relative to the rod portion about the longitudinal direction prior to seating the intramedullary alignment rod within the femur, the sizing guide block having thereon longitudinally projecting foot means for engaging the posterior distal femur when the intramedullary alignment rod is seated within the femur with the rod portion projecting in the longitudinal direction from the distal femur;

seating the intramedullary alignment rod within the femur while permitting movement of the sizing guide block upon the rod portion in an altitudinal direction relative to the rod portion, and precluding rotation of the sizing guide block relative to the rod portion, to engage the foot means with the posterior distal femur as the intramedullary alignment rod is seated within the femur, thereby locating the sizing guide block in a sizing position with respect to the distal femur;

locking the sizing guide block against altitudinal movement relative to the rod portion when the sizing block is in the sizing position, subsequent to seating of the intramedullary alignment rod within the femur, wherein the foot means of the sizing guide block is located against the posterior distal femur, such that the sizing guide block is locked in place upon the intramedullary alignment rod in the sizing position; and guiding a cutting instrument with a posterior femoral cutting guide on the sizing guide block to establish a preliminary posterior femoral cut when the sizing guide block is in the sizing position.

10. The invention of claim 9 including:

mounting a stylus upon the sizing guide block for unrestricted movement in altitudinal directions relative to the sizing guide block, and moving the stylus in altitudinal directions relative to the sizing guide block to locate the stylus against the anterior cortex with the stylus mounted upon the sizing guide block; and observing an indication on the sizing guide block, when the sizing guide block is in the sizing position and the stylus is located against the anterior cortex, indicative of the size of the femoral knee prosthesis to be implanted.

11. The invention of claim 10 including:

locating a distal femoral resection guide on the sizing guide block to determine the location of the distal femoral resection guide on the distal femur;

subsequently securing the distal femoral resection guide at the determined location on the distal femur; and subsequently guiding a cutting instrument with the distal femoral resection guide to establish a distal femoral cut.

12. The invention of claim 11 including:

locating a femoral cutting guide upon the distal femur as prepared with the preliminary posterior cut and the distal femoral cut;

securing the located femoral cutting guide upon the distal femur; and guiding a cutting instrument with the secured femoral cutting guide to establish a final posterior cut, an anterior cut, an anterior chamfer cut and a posterior chamfer cut.

13. The invention of claim 10 including moving the stylus in a sweeping movement in a lateral direction across the anterior cortex, while the stylus is free to move in the altitudinal directions relative to the sizing guide block in response to the sweeping movement;

observing the indication on the sizing guide block as the indication moves along a scale of size designations during the sweeping movement of the stylus.

14. The invention of claim 13 including:

adjusting the altitudinal position of the sizing guide block relative to the rod portion of the intramedullary alignment rod until the sizing guide block is in an adjusted sizing position wherein the indication observed on the sizing guide block is maintained within only one of the size designations as the stylus is moved through the sweeping movement; and guiding a cutting instrument with the posterior femoral cutting guide on the sizing guide block to establish a further posterior femoral cut when the sizing guide block is in the adjusted sizing position.

15. The invention of claim 14 including:

locating a distal femoral resection guide on the sizing guide block to determine the location of the distal femoral resection guide on the distal femur;

subsequently securing the distal femoral resection guide at the determined location on the distal femur; and subsequently guiding a cutting instrument with the distal femoral resection guide to establish a distal femoral cut.

16. The invention of claim 15 including:

locating a femoral cutting guide upon the distal femur as prepared with the further posterior cut and the distal femoral cut;

securing the located femoral cutting guide upon the distal femur; and guiding a cutting instrument with the secured femoral cutting guide to establish a final posterior cut, an anterior cut, an anterior chamfer cut and a posterior chamfer cut.

17. The invention of claim 9 including adjusting the angular orientation of the foot means on the sizing guide block to set the longitudinal position of the foot means relative to the sizing guide block for selecting a particular rotational position for the femoral knee prosthesis to be implanted.

\* \* \* \* \*